US00PP31108P2

(12) United States Plant Patent
Bradford et al.

(10) Patent No.: US PP31,108 P2
(45) Date of Patent: Nov. 26, 2019

(54) NECTARINE TREE NAMED 'PEARLICIOUS XVIII'

(50) Latin Name: *Prunus persica*
Varietal Denomination: Pearlicious XVIII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/350,706

(22) Filed: Dec. 26, 2018

(51) Int. Cl.
*A01H 5/08* (2018.01)
*A01H 6/74* (2018.01)

(52) U.S. Cl.
USPC ..... Plt./188
CPC ..... *A01H 6/74* (2018.05)

(58) Field of Classification Search
USPC ..... Plt./188
CPC ..... A01H 5/0856
See application file for complete search history.

(56) References Cited

U.S. PATENT DOCUMENTS

PP25,828 P3 8/2015 Bradford

*Primary Examiner* — Kent L Bell

(57) ABSTRACT

The present invention relates to a new and distinct variety of nectarine tree, *Prunus persica*, broadly characterized by a large size, vigorous, hardy, self-fertile, productive and regular bearing tree. The variety blooms during the mid season and requires about 550 chilling hours. The fruit matures under the ecological conditions described in late August, with first picking on Aug. 21, 2018. The fruit is uniform, medium in size, sub-acidic and very sweet in flavor, oblate in shape, clingstone in type, firm in texture, white in flesh color, mostly red in skin color, and has a bitter tasting kernel.

1 Drawing Sheet

Botanical classification: *Prunus persica.*
Variety denomination: 'PEARLICIOUS XVIII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Pearlicious XVIII'.

In 2007 we made a first generation hybridization using '10G523' (unpatented) nectarine as the selected seed parent and '26P994' (unpatented) nectarine as the selected pollen parent. Upon reaching maturity the fruit of this hybridization was gathered, and the seeds were removed, cracked; stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2012 we selected the present variety as a single tree trom the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, '10G523' (unpatented) nectarine, by being self-fertile and by producing nectarines that are white in flesh color, that are clingstone in type, that are medium to large in size, and that ripen in mid to late August, but is distinguished from it by having a small instead of large blossom and by producing fruit that is much redder in skin color, that is substantially sweeter in flavor, and that is firmer in texture.

The present variety is similar to its pollen parent, '26P994' (unpatented) nectarine, by being self-fertile and by producing nectarines that are mostly red in skin color, clingstone in type, and sub-acidic in flavor, but is quite distinguished from it by producing fruit that is somewhat smaller in size, that is white instead of yellow in flesh color, and that ripens about forty days later.

The present variety is most similar to 'Pearlicious XVI' (U.S. Plant Pat. No. 25,828) nectarine by being self-fertile, by requiring about 550 chilling hours, by blooming in the mid season, by having globose leaf glands, by having a bitter kernel, and by producing nectarines that are white in flesh color, that are clingstone in type, that are firm in texture, that are sweet and sub-acidic in flavor, and that ripen in mid August, but is distinguished therefrom by having a larger and more vigorous tree, by having a small instead of large blossom, and by producing nectarines that are somewhat smaller in size, that are a fuller red in skin color, and that are oblate instead of globose to elongated in shape.

SUMMARY OF VARIETY

In summary, the present nectarine variety is characterized by a large size, vigorous, hardy, self-fertile, productive and regular bearing tree. The variety blooms during the mid season and requires about 550 chilling hours. The fruit matures under the ecological conditions described in late August, with first picking on Aug. 21, 2018. The fruit is uniform, medium in size, sub-acidic and very sweet in flavor, oblate in shape, clingstone in type, firm in texture, white in flesh color, mostly red in skin color, and has a bitter tasting kernel.

DRAWING

The accompanying photograph consists of four whole fruits positioned to display the characteristics of the skin color and form, one divided fruit to reveal the flesh and stone, typical leaves, and two insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Aug. 26, 2018, on the original tree during its eleventh growing season. The blossom and flower descriptions were made the previous blooming season. All major color code designations are by reference to the Inter-Society Color Council, National Bureau of Standards. Common color names are also used occasionally.

PARENTAGE

Seed parent: '10G523' (unpatented) nectarine.
Pollen parent: '26P994' (unpatented) nectarine.

TREE

Size: Large, reaching and maintaining a height of 12' [3.66 m.] and a spread of 10' [3.05 m.] after eleven growing seasons utilizing typical dormant pruning.

Vigor: Vigorous, responding about average to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: About 550 hours.

Leaf bud burst: Medium to late, during the end of flowering.

Trunk:

- *Size.*—Medium, reaching a maximum diameter of 5" [127 mm.] after the eleventh growing season.
- *Texture.*—Medium.
- *Bark color.*—A Grayish yellowish brown [80. gy.yBr] and Moderate yellowish brown [77. m.yBr] variegation with Dark yellowish brown [78. d.yBr] crevices present.
- *Lenticels.*—Approximate Number Per Square Inch: 8. Color: Light grayish yellowish brown [79. l.gy.yBr]. Average Size: ¼" [6.4 mm.] in length. The width is typically one fourth as much as the length. Shape: Eye-shaped.

Branches:

- *Size.*—Medium, diameter of main scaffold is 3½" [88.9 mm.] measured 12" above the crotch, diameter of limb is 1¼" [31.8 mm.] measured 12" above the first fork.
- *Texture.*—Smooth to medium on first and second year wood, increasing in roughness with age.
- *Color.*—1st Year Wood Topside: Grayish red [19. gy.R]. 1st Year Wood Underside: Brilliant yellow green [116. brill.YG]. 2nd Year Wood: A Moderate brown [58. m.Br] and Light brown [57. l.Br] variegation.
- *Lenticels.*—Number Per Square Inch: About 45 on second year wood. Color: Light yellowish brown [76. l.yBr]. Average Size: Medium, 1/16" [1.6 mm.] in length. The width is typically one fourth as much as the length. Shape: Eye-shaped.

Leaves:

- *Size.*—Large. Average Length: 6 1/16" [154 mm.]. Average Width: 1⅝" [41.3 mm.].
- *Arrangement.*—Alternate.
- *Thickness.*—Medium.
- *Form.*—Elliptical.
- *Apex.*—Acuminate.
- *Base.*—Acute, with an average base angle of 75 degrees.
- *Surface.*—Smooth on both sides.
- *Color.*—Dorsal Surface: Moderate olive green [125. m.OlG]. Ventral Surface: Moderate yellow green [120. m.YG].
- *Red Midvein.*—Absent.
- *Margin.*—Finely serrate.
- *Venation.*—Pinnately net veined.
- *Petiole.*—Average Length: 5/16" [7.9 mm.]. Average Thickness: 1/16" [1.6 mm.]. Color: Strong yellow green [117. s.YG].
- *Stipules.*—Number: 2 per leaf, up to 6 per growing tip. Average Length: ¼" [6.4 mm.]. Color: Vivid yellow green [115. v.YG] becoming Moderate brown [58. m.Br] with age.
- *Glands.*—Number: 2 to 4 per leaf. Position: Alternate, first pair is located at the intersection of petiole and base of blade. Form: Globose. Size: Medium, about 1/32" [0.8 mm.] in diameter. Color: Light yellow green [119. l.YG] becoming Dark olive brown [96. d.OlBr] with age.
- *Leaf buds.*—Pointed.

Flower buds:

- *Hardiness.*—Hardy, with respect to central California blooming season.
- *Diameter.*—Typically ⅜" [9.5 mm.] 1 week before bloom.
- *Length.*—Typically ⅝" [15.9 mm.] 1 week before bloom.
- *Form.*—Not appressed.
- *Surface.*—Slightly pubescent.
- *Tip color.*—Moderate purplish pink [250. m.pPk].

Flowers: Perfect, complete, perigynous, usually a single pistil, about thirty stamens, five sepal and petal locations alternately positioned.

*Type.*—Non-showy, small.

*Average flower diameter.*—1" [25.4 mm.].

*Average flower depth.*—5/16" [7.9 mm.] when fully open.

*Average pedicel length.*—¼" [6.4 mm.].

*Number of petals.*—Mostly five, extra petal fragments occasionally observed.

*Petal arrangement.*—Not overlapping, separated.

*Petal shape.*—Oval to cuneate.

*Petal margin.*—Entire, wavy.

*Average petal diameter.*—¼" [6.4 mm.].

*Average petal length.*—7/16" [11.1 mm.].

*Petal apex.*—Rounded to slightly obovate.

*Petal base.*—Acute to rounded.

*Petal color.*—Light pink [4. l.Pk] toward the apex, Strong pink [2. s.Pk] toward the base on both sides.

*Anther color.*—Deep reddish orange [36. deep rO] at bloom onset.

*Pollen.*—Anthers produce an abundance of Very yellow [82. v.Y] pollen.

*Stigma color.*—Light yellow green [119. l.YG].

*Stigma position.*—Typically located about even with the nearby anthers.

*Stamen position.*—Typically located about 1/16" [1.6 mm.] above the petals.

*Ovary.*—Non-pubescent.

*Sepal color.*—Dark purplish red [259. d.pR] on the outer surface. The inner surface is a somewhat translucent Pinkish white [9. pkWhite] with both Grayish purplish red [262. gy.pR] and Vivid yellow green [115. v.YG] areas visible.

*Sepal length.*—3/16" [4.8 mm.].

*Sepal width.*—5/32" [4.0 mm.].

*Sepal apex.*—Rounded to elliptical to match the sepal length and width.

*Sepal margin.*—Fairly smooth.

*Average pistil length.*—11/16" [17.5 mm.].

*Average stamen length.*—7/16" [11.1 mm.].

*Fragrance.*—Moderate.

*Blooming period.*—Medium when compared to other varieties, about the same day as 'Grand Bright' (U.S. Plant Pat. No. 16,494) nectarine.

*Onset of bloom.*—One percent on Feb. 24, 2018.

*Date of full bloom.*—Mar. 3, 2018.

*Duration of bloom.*—One to two weeks, dependent on ambient temperature.

*Bloom density.*—Medium.

*Number per cluster.*—1 to 3 with single flowers most common.

FRUIT

Maturity when described: Shipping ripe, Aug. 26, 2018.

Date of first picking: Aug. 21, 2018.

Date of last picking: Aug. 30, 2018.

Size: Uniform, medium.

*Average diameter axially.*—2¾" [69.9 mm.].

*Average diameter across suture plane.*—3⅛" [79.4 mm.].

*Average diameter across cheek plane.*—3" [76.2 mm.].

*Typical weight.*—8.5 ounces [241 grams].

Form: Uniform, oblate, symmetrical.

*Longitudinal section form.*—Oblate.

*Axial view.*—Round.

Suture: A very shallow trough extending from the base, along the side, and ending about ½" [12.7 mm.] beyond the pistil point.

*Near the base.*—A shallow trough.

*Along the side.*—A very shallow trough.

*Near the apex.*—A moderate v-shaped groove.

Ventral surface: Rounded, lipped toward the apex on both sides.

Lips: Fairly equal.

Cavity: Flaring, circular, suture showing on one side, Brilliant greenish yellow [98. brill.gY] stem markings present.

*Depth.*—½" [12.7 mm.].

*Breadth.*—⅞" [22.2 mm.].

Base: Truncate, slightly cordate if viewed parallel to the suture.

Apex: Rounded, cordate when viewed parallel to the suture.

Pistil point: Apical, negligible in length, depressed within the suture.

Stem: medium.

*Average length.*—⅜" [9.5 mm.].

*Average width.*—3/16" [4.8 mm.].

Skin:

*Thickness.*—Medium.

*Surface.*—Smooth.

*Tenacity.*—Tenacious to the flesh.

*Astringency.*—Non-astringent.

*Tendency to crack.*—None observed.

*Color.*—Dark red [16. d.R] over a Pale greenish yellow [104. p.gY] background with moderate Light greenish yellow [101. l.gY] freckling toward the apex.

Flesh:

*Color.*—White [263. White] with Vivid red [11. v.R] streaking next to the stone.

*Surface of pit cavity.*—Covered with Vivid deep red [14. v.deep R] broken fibers when twisted away from the stone.

*Amygdalin.*—Scarce.

*Juice.*—Moderate, rich.

*Texture.*—Firm, crisp.

*Fibers.*—Few, fine, tender.

*Ripens.*—Fairly even, earliest at the shoulders.

*Flavor.*—Sub-acidic, very sweet, typically 20 brix.

*Aroma.*—Very slight.

*Eating quality.*—Excellent.

STONE

Type: Clingstone.

Form: Oval.

Hilum: Narrow, oblong.

Base: Truncate.

Apex: Acute to rounded.

Sides: Equal.

Tip: Sharp, 1/64" [0.4 mm.] in length.

Surface: Irregularly furrowed toward the apex, pitted toward the base.

Ridges: Jagged.

External color: Vivid dark red [17. v.d.R] when first removed.

Pit wall color when cracked: Grayish reddish brown [46. gy.rBr].

Cavity surface color: Strong brown [55. s.Br].

Average pit wall thickness: ¼" [6.4 mm.].
Average length: 1⅜" [34.9 mm.].
Average width: 1" [25.4 mm.].
Average breadth: ⅞" [22.2 mm.].
Tendency to split: None observed.
Kernel:
*Form.*—Oval.
*Skin color.*—Brownish orange [54. brO].
*Pellicle color.*—Dark brown [59. d.Br].
*Vein color.*—Deep brown [56. deep Br].
*Taste.*—Bitter.
*Viable.*—Yes.
*Average length.*—11/16" [17.5 mm.].
*Average width.*—7/16" [11.1 mm.].
*Amygdalin.*—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'Pearlicious XVI' (U.S. Plant Pat. No. 25,828) nectarine by being self-fertile, by requiring about 550 chilling hours, by blooming in the mid season, by having globose leaf glands, by having a bitter kernel, and by producing nectarines that are white in flesh color, that are clingstone in type, that are firm in texture, that are sweet and sub-acidic in flavor, and that ripen in mid August, but is distinguished therefrom by having a larger and more vigorous tree, by having a small instead of large blossom, and by producing nectarines that are somewhat smaller in size, that are a fuller red in skin color, and that are oblate instead of globose to elongated in shape.

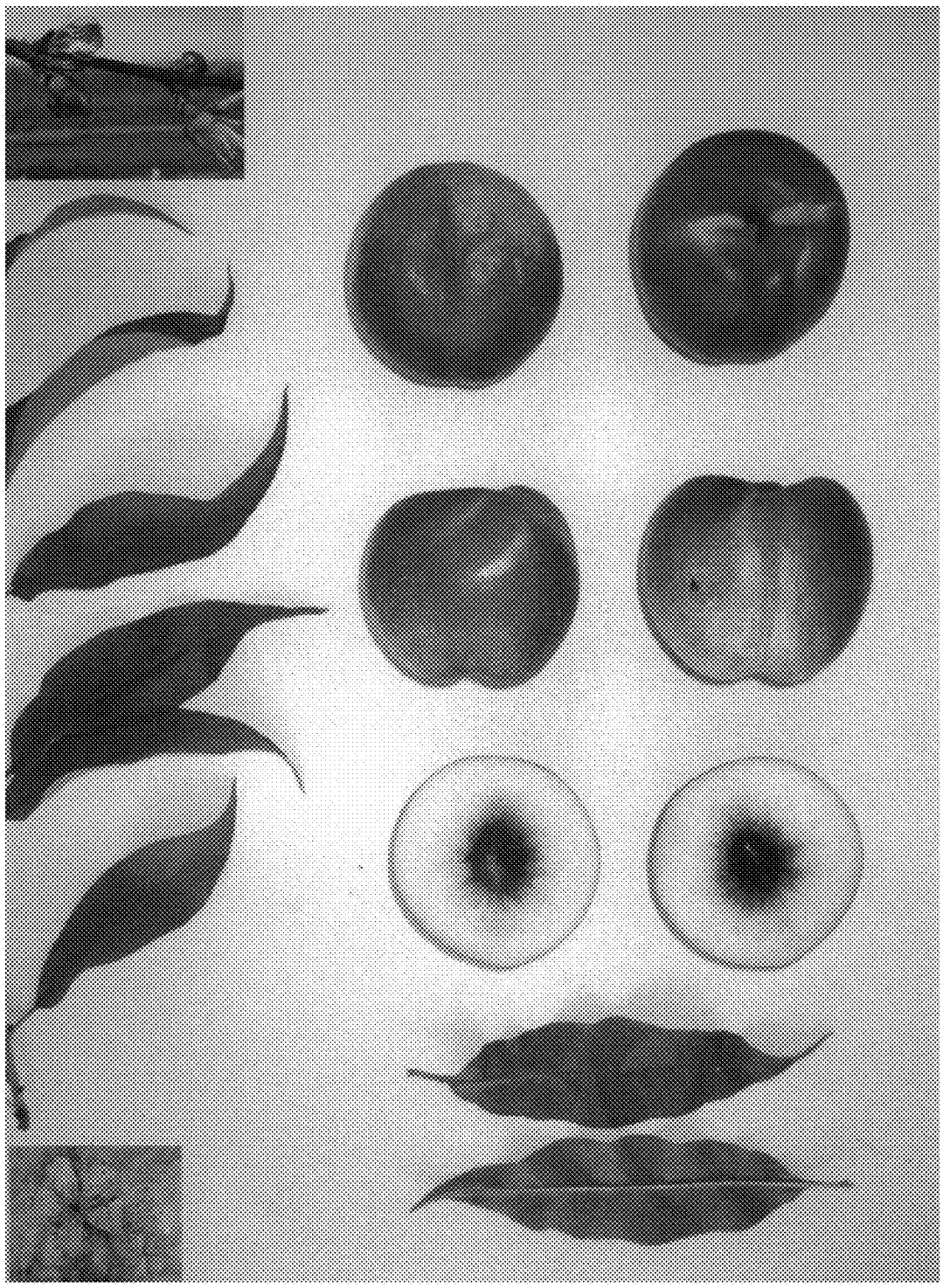

* * * * *